United States Patent
Singh et al.

(12)

(10) Patent No.: US 6,451,302 B1
(45) Date of Patent: *Sep. 17, 2002

(54) PARENTERAL WATER-MISCIBLE NON-INTENSELY COLORED INJECTABLE COMPOSITION OF NON-STEROIDAL ANTI-INFLAMMATORY DRUGS

(75) Inventors: Amarjit Singh; Rajesh Jain, both of New Delhi (IN)

(73) Assignee: Panacea Biotec Limited (ID)

( * ) Notice: Subject to any disclaimer, the term of this patent is extended or adjusted under 35 U.S.C. 154(b) by 38 days.

This patent is subject to a terminal disclaimer.

(21) Appl. No.: 09/641,810

(22) Filed: Aug. 17, 2000

Related U.S. Application Data

(63) Continuation of application No. 09/120,099, filed on Jul. 21, 1998.

(30) Foreign Application Priority Data

Jan. 12, 1998 (IN) .................................................. 056/98

(51) Int. Cl.⁷ ............................ A61K 31/04; A61K 9/08
(52) U.S. Cl. ...................... 424/78.05; 424/449; 514/605
(58) Field of Search ....................... 514/605; 424/78.05, 424/449

(56) References Cited

U.S. PATENT DOCUMENTS 5,716,609 A * 2/1998 Jain et al. ................. 424/78.05

FOREIGN PATENT DOCUMENTS

| IN | 1389/DEL/95 | * | 7/1995 |
| IN | 2046/DEL/95 | * | 11/1995 |
| IN | 2047/DEL/95 | * | 11/1995 |
| IN | 2048/DEL/95 | * | 11/1995 |
| WO | WO 99/41233 | | 8/1999 |

* cited by examiner

*Primary Examiner*—Ralph Gitomer
*Assistant Examiner*—Devesh Khare
(74) *Attorney, Agent, or Firm*—Akerman Senterfitt

(57) ABSTRACT

A Parenteral Water-miscible non-intensely coloured injectable composition of Non-steroidal anti-inflammatory drugs is disclosed. The invention utilizes solubilization techniques to achieve sufficiently high concentrations of Nimesulide suitable to deliver therapeutic doses in conveniently small volumes using water and without any salt form or complexing agent of Nimesulide. In the composition of the invention all the ingredients of the base are hydrophillic. The hydrophillic base serves the advantage of better miscibility with body fluids, faster drug disposition and better compatibility with the tissue environment.

8 Claims, No Drawings

PARENTERAL WATER-MISCIBLE NON-INTENSELY COLORED INJECTABLE COMPOSITION OF NON-STEROIDAL ANTI-INFLAMMATORY DRUGS

This is a Continuation of application Ser. No. 09/120,099, filed Jul. 21, 1998.

The present invention relates to novel therapeutic non intensely coloured, water miscible injectable analgesic pharmaceutical compositions of Non-steroidal anti-inflammatory drugs and a process for the manufacture of such drugs. The analgesic injectable composition is very useful in mammals particularly in humans for the treatment of acute painful conditions like post operative trauma, pain associated with cancer, sports injuries, migraine headache, neurological pain, pain associated with sciatica and spondylitis. For these indications some modified route of administrations may also be construed.

BACKGROUND OF THE INVENTION

Non-steroidal anti-inflammatory drugs such as those belonging to the category of Cyclo-oxygenase-2 inhibitors including Nimesulide are highly hydrophobic compounds and readily precipitate even in the presence of minor amounts of water.

It is therefore very difficult to formulate Non-steroidal anti-inflammatory drugs which are inhibitors of Cyclo-oxygenase-2 as an injection for intramuscular or intravenous use.

In the past, efforts have been made to make an injectable composition of Nimesulide.

An injectable formulation of Nimesulide has been reported in the prior art PCT Patent No. WO 95/34533 which utilizes a salt form of Nimesulide with L-lysine which is in turn further complexed with cyclodextrins which may be dissolved in water to give an injectable preparation. The maximum solubility achieved by this injectable composition was reported to be 2.4 mg/ml which is not sufficient for intramuscular administration as it would require very large volumes to administer therapeutic doses. Moreover making a salt form of Nimesulide and then combining with Cyclo-dextrins not only makes the process cumbersome but also increases the cost of the formulations.

Another reference (Daffonchio. L et al. Inflammatory Research 45:259–264; 1995) wherein Nimesulide is dissolved in saline for intravenous administration for experimental studies in animals also describes only very dilute solutions which cannot deliver therapeutic doses in humans.

The disadvantages of WO 95/34533 and problems associated therewith were overcome by the invention described in U.S. Pat. No. 5,688,829 (Corresponding Korean Application No. 96-48013, Australian Application No. 67993/96 and Japanese Patent Application No. 8-290585, all pending) by the inventors of the present invention.

This invention utilizing solubilization techniques was able to achieve sufficiently high concentrations of Nimesulide suitable to deliver therapeutic doses in conveniently small volumes using a base which was oily in nature without using water and without any salt form or complexing agents of Nimesulide.

The present invention comprises a composition wherein all the ingredients of the base are hydrophilic. The hydrophilic base serves the advantage of better miscibility with body fluids, faster drug disposition and better compatibility with the tissue environment.

It is an objective of the present invention to provide an injectable analgesic hydrophilic composition of Non-steroidal anti-inflammatory drugs which are non-intensely coloured having better miscibility with body fluids. Such hydrophilic compositions described herein can be administered by intravenous routes also in addition to intramuscular route.

It is another objective of the present invention to provide a novel process for the preparation of a parenteral hydrophilic injectable composition of NSAIDs.

SUMMARY OF THE INVENTION

The invention comprises a novel injectable aqueous miscible composition of Cyclo-oxygenase-2 inhibitors such as Nimesulide which comprises:

1. Cyclooxygenase inhibitors
2. Alkyl amides/Alkyl sulphoxides or pyrrolidones
3. Glycols
4. 0 to 20% of water.

DETAILED DESCRIPTION OF THE INVENTION

The Cyclo-oxygenase-2 inhibitors belonging to the category of NSAIDs are selected from the group comprising of Nimesulide, Nabumetone, Tapoxalin and Flosulide and derivatives thereof.

The Alkyl amides/Alkyl sulphoxides or pyrrolidones in accordance with the present invention are selected from the group- Dimethylacetamide, Dimethylformamide and Dimethylsulphoxide of N-Methyl Pyrrolidone.

The glycols in accordance with the present invention are selected from the group Polyethylene Glycol MW 200 to 6000, Propylene Glycol, Hexylene glycols, Butylene glycols and Glycol derivatives such as Polyethylene Glycol 660 hydroxy stearate (commercialy available as Solutrol HS15).

Beside the composition may also comprise the following conventional additional ingredients—Surfactants, hydrophilic polymers, solubility enhancing agents i.e. Glycerine, various grades of Polyethylene oxides, β-cyclodextrins like sulfo butyl ether-β-cyclodextrin, Transcutol and Glycofurol, tonicity adjusting agents, local anesthetics, pH adjusting agents and buffers.

Preferably the Non-steroidal anti-inflammatory drug belonging to the category of Cyclo-oxygenase-2 inhibitors is Nimesulide and derivatives thereof and is present in the composition from 0.1 to 10% w/v.

More preferably Nimesulide is present from 0.5 to 8% w/v.

More preferably Nimesulide is present in the composition from 1.2 to 4.8% w/v. Preferably the composition in accordance with the present invention comprises Alkyl amides/Alkyl sulphoxides or pyrrolidones from 2.0% to 95% w/v.

More preferably the composition comprises Alkyl amides/Alkyl sulphoxides or pyrrolidones from 5% to 90%.

More preferably Alkyl amides/Alkyl sulphoxides or pyrrolidones are present from 10% to 20% w/v.

Preferably Glycols are present in the composition from 0.1% to 95% w/v.

In a preferred embodiment of the invention there is described an injectable water miscible non-intensely coloured analgesic pharmaceutical composition of Nimesulide which comprises:

| | |
|---|---|
| Nimesulide from | 0.1 to 10% w/v |
| Dimethylacetamide from | 2.0 to 90% w/v |

-continued

| | |
|---|---|
| Polyethylene Glycols from | 0.1 to 95% w/v. |
| Water from | 0 to 20% w/v. |

In a preferred embodiment, the drug is dissolved in an oily phase and emulsified in aqueous phase using surfactants including lecithins leading to microemulsion or emulsion suitable for intravenous use.

In accordance with the present invention there is also described a novel process for the manufacture of an injectable water miscible analgesic pharmaceutical composition of a NSAID.

The process comprises:

a) Dissolving Nimesulide in Dimethylacetamide and adding thereto freshly distilled Benzyl Alcohol and stirring. Adding subsquently to the solution Polyethylene Glycol 400 to the above solution and mixing. Adding to the solution Hydrochloric Acid solution slowly with stirring and then adding to a Propylene Glycol to make volume upto 95% of the actual batch size. The solution formed pH between 2.0 to 3.0. If it is not in this range then adjust it either with Sodium Hydroxide (10% w/v solution) or Hydrochloric Acid solution. Make up the final volume with Propylene Glycol.

b) Filter the resultant solution through 0.45 micron nylon membrane filter using a 6 micron glass fibre pre-filter. Collect the filtered solution in a clean fibre-free vessel. Fill the solution in fiber-free sterile 2 ml amber USP Type 1 glass ampoules with pre and post filling nitrogen flushing.

c) Sterilize the ampoules by autoclaving. Optically inspect all the ampoules and after release by Quality Control Deptt. label the good ones.

The invention will now be described by the following examples for injectable analgesic composition of NSAIDs.

Example 1

| | % w/v |
|---|---|
| Nimesulide | 2% |
| Dimethylacetamide | 10% |
| Water | 1% |
| Benzyl Alcohol | 4% |
| BHA (Butylated Hydroxy Anisole) | 0.1% |
| Polyethylene Glycol 300 | q.s. to 100%. |

Example 2

| | % w/v |
|---|---|
| Flosulide | 1% |
| N-methyl pyrrolidone | 5% |
| Dimethylacetamide | 5% |
| Polyethylene Glycol 400 | 30% |
| Water | 5% |
| Benzyl Alcohol | 2% |
| α-tocopheryl acetate | 0.05 |
| Propylene Glycol | q.s. - 100% |

Example 3

| | % w/v |
|---|---|
| Nimesulide | 1.2% |
| Dimethylacetamide | 10% |
| Benzyl Alcohol | 4% |
| Propylene Glycol | q.s. - 100%. |

Example 4

| | % w/v. |
|---|---|
| Nimesulide | 10% |
| Benzyl Alcohol | 2% |
| Dimethylacetamide | q.s - 100% |

The composition is of the types that has to be diluted prior to use with suitable diluents.

Example 5

| | % w/v |
|---|---|
| Nimesulide | 0.5% |
| Benzyl Alcohol | 2% |
| Lecithin (Lipoid E-80) | 1% |
| Dimethylacetamide | 10% |
| Water | 2% |
| Polyethylene Glycol 300 | q.s - 100% |

On affecting Acute Toxicity studies on Balb/C Mice by intra peritoneal route the $LD_{50}$ was found to be 160 mg/kg, $ED_{50}$=3 mg/kg with therapeutic index=53.3 in mice. This demonstrates high safety of the present invention. The injectable analgesic composition, according to the present invention, on preliminary animals and preclinical trails as shown to posses marked analgesic activity. Further it has been found to non-toxic even on repeated applications on same site.

No incidence of tissue necrosis or any other side effect was observed. The analgesic dose range from 0.1 mg/kg to 8.4 mg/kg.

Since many apparently different embodiments of the present invention could be made without departing from the spirit and scope thereof, it is intended that the description of the invention herein be interpreted as being illustrative only and not limiting in any manner whatsoever.

We claim:

1. A parenteral, water-miscible composition comprising:
   nimesulide from 0.1 to 10% w/v;
   benzyl alcohol;
   a substance selected from the group consisting of dimethylacctamide, dimethylformamide, dimethylsulphoxide, and N-methyl pyrrolidone from 2.0 to 90% w/v; and
   a glycol selected from the group consisting of polyethylene glycol MW 200 to 600, propylene glycol, hexylene glycol, butylene glycol, and polyethylene glycol 660 hydroxy stearate from 0.1 to 95% w/v,
   wherein the composition is injectable.

2. The composition of claim 1 wherein the nimesulide content is from 0.25%–10% w/v.

3. The composition of claim 1 wherein the glycol is polyethylene glycol 300 from about 0.1 to 95% w/v.

4. The composition of claim 2 wherein the glycol is polyethylene glycol 300 from about 0.1 to 95% w/v.

5. A parenteral, water-miscible composition consisting essentially of:
   nimesulide from 0.1 to 10% w/v;
   benzyl alcohol from 2 to 4% w/v;
   a substance selected from the group consisting of dimethylacetamide, dimethylformamide, dimethylsulphoxide, and N-methyl pyrrolidone from 2.0 to 90% w/v; and
   a glycol selected from the group consisting of polyethylene glycol MW 200 to 600, propylene glycol, hexylene glycol, butylene glycol, and polyethylene glycol 660 hydroxy stearate from 0.1 to 95% w/v,
   wherein the composition is injectable.

6. The composition of claim 5 wherein the nimesulide content is from 0.25%–10% w/v.

7. The composition of claim 5 wherein the glycol is polyethylene glycol 300 from about 0.1 to 95% w/v.

8. The composition of claim 6 wherein the glycol is polyethylene glycol 300 from about 0.1 to 95% w/v.

* * * * *